(12) United States Patent
Erusalimsky et al.

(10) Patent No.: US 9,017,936 B2
(45) Date of Patent: Apr. 28, 2015

(54) ASSAYS FOR AGENTS AFFECTING MEGAKARYOCYTE DEVELOPMENT

(75) Inventors: Jorge D. Erusalimsky, London (GB); Maninder Ahluwalia, Cardiff (GB)

(73) Assignees: Shire Human Genetic Therapies, Inc., Lexington, MA (US); University of Wales Institute, Cardiff, Cardiff (GB)

( * ) Notice: Subject to any disclaimer, the term of this patent is extended or adjusted under 35 U.S.C. 154(b) by 513 days.

(21) Appl. No.: 12/898,590

(22) Filed: Oct. 5, 2010

(65) Prior Publication Data

US 2011/0111966 A1   May 12, 2011

Related U.S. Application Data

(60) Provisional application No. 61/249,176, filed on Oct. 6, 2009.

(51) Int. Cl.
*C12Q 1/68* (2006.01)
*G01N 33/53* (2006.01)
*G01N 33/50* (2006.01)

(52) U.S. Cl.
CPC ........ *C12Q 1/6883* (2013.01); *C12Q 2600/136* (2013.01); *C12Q 2600/158* (2013.01); *G01N 33/5011* (2013.01)

(58) Field of Classification Search
None
See application file for complete search history.

(56) References Cited

U.S. PATENT DOCUMENTS

2006/0280684 A1   12/2006  Lund et al.
2008/0014583 A1*  1/2008   Montminy et al. ............... 435/6

FOREIGN PATENT DOCUMENTS

WO   WO 2007/085958   8/2007

OTHER PUBLICATIONS

Meng and Limbach (Briefings in Functional Genomics and Proteomics, 2006, vol. 5, No. 1, pp. 87-95).*
Santos et al (Journal of Neuroscience Research, 2008. vol. 86, pp. 3684-3692).*
Du et al., "TRB3: A tribbles Homolog That Inhibits Akt/PKB Activation by Insulin in Liver," *Science* 300:1574-1577 (2003).
Erusalimsky et al,, "Upregulation of Human Tribbles Homologue 3 (TRB3) by Anagrelide: A Novel Molecular Marker for the Discovery of Candidate Platelet Lowering Agents," *Haematologica* 95[suppl. 2]:162, abs. 0399 (2010).
Garzon et al., "MicroRNA fingerprints during human megakaryocytopoiesis," *Proc. Natl Acad Sci USA* 103:5078-5083 (2006).
Sathyanarayana et al., "EPO receptor circuits for primary erythroblast survival," *Blood* 111:5390-5399 (2008).
Uzan, G. et al., "Hematopoletic Differentiation of Embyonic Stem Cells: An in Vitro Model to Study Gene Regulation During Megakaryocytopoiesis," *Stem Cells* 14:194-199 (1996).
Vandesompele et al., "Accurate normalization of real-time quantitative RT-PCR data by geometric averaging of multiple internal control genes," *Genome Biol* 3(7): RESEARCH0034.1-0034.11 (2002).
Wang et al., "Comparison of the biological activities of anagrelide and its major metabolites haematopoietic cell cultures," *Brit. J Pharmacol.* 146(3):324-332 (2005).
Erusalimsky et al., "Upregulation of Human Tribbles Homologue 3 (TRB3) by Anagrelide: A Novel Molecular Marker for the Discovery of Candidate Platelet Lowering Agents," *Presentation at European Hematology Association Annual Conference*, Jun. 10-13, 2010.
Oro T et al: "Human TRB3 is upregulated in stressed cells by the induction of translationally efficient mRNA containing a truncated 5'-UTR", Gene, 444(1-2): 24-32 (2009).
Horikawa et al: "Markedly reduced expression of platelet c-mpl receptor in essential thrombocythemia.", Blood, 90(10):4031-4038 (1997).
Tanja Ficko: "Platelet glycoprotein lila gene expression in normal and malignant megakaryopoiesis", Annals of Hematology, 87(2): 131-137 (2007).
European Search Report in Application EP 10822553.3, dated Mar. 14, 2013.

* cited by examiner

*Primary Examiner* — Celine Qian
(74) *Attorney, Agent, or Firm* — Choate, Hall & Stewart LLP; Fangli Chen; Rolando Medina

(57) ABSTRACT

Methods and kits for identifying candidate anti-megakaryocyte agents are disclosed.

40 Claims, 12 Drawing Sheets

ASSAYS FOR AGENTS AFFECTING MEGAKARYOCYTE DEVELOPMENT

RELATED APPLICATIONS

This application claims the benefit of, U.S. Provisional Application No. 61/249,176, filed Oct. 6, 2009. The entire teachings of the above application are incorporated herein by reference.

BACKGROUND OF THE INVENTION

Myeloproliferative disorders are a group of conditions that cause blood cells, e.g., platelets, white blood cells, and red blood cells, to grow or differentiate abnormally in the bone marrow. Myeloproliferative disorders typically include polycythemia vera, primary myelofibrosis, chronic myelogenous leukemia, and essential thrombocythemia. Polycythemia vera occurs when the bone marrow produces too many red blood cells. In cases of primary myelofibrosis (also known as idiopathic myelofibrosis or myeloid metaplasia), the bone marrow produces too much collagen and is replaced by fibrous tissue, reducing the ability of bone marrow to produce blood cells. Chronic myelogenous leukemia (CML) is a type of cancer of the bone marrow that produces too many granulocytes and their precursors in the bone marrow. Essential thrombocythaemia (also known as primary thrombocytosis) occurs when the body produces too many platelet cells, which help blood to clot; clots can block blood vessels, leading to heart attack or stroke. In some cases essential thrombocythemia is a progressive disorder which may evolve into acute myeloid leukemia or myelofibrosis.

Among the treatments for essential thrombocythemia is anagrelide ((6,7-dichloro-1,5-dihydroimidazo (2,1-b) quinazolin-2(3H)-one). Anagrelide is a potent inhibitor of phosphodiesterase type III. Anagrelide also inhibits the development of megakaryocytes and consequently platelet production. In certain patients anagrelide may have undesirable side effects ranging from mild to serious. Accordingly, additional agents that can inhibit the differentiation of megakaryocytes may offer improved therapeutic options.

SUMMARY OF THE INVENTION

One embodiment relates to a method of identifying a candidate anti-megakaryocyte agent comprising incubating a cell capable of expressing TRB-3 in the presence of a test agent; and measuring expression of TRB-3, wherein a test agent which increases expression (e.g., to a statistically significant degree) of TRB-3 relative to an appropriate control is a candidate anti-megakaryocyte agent. An appropriate control may be, for example, the level of expression of TRB-3 in the absence of the test agent or the level of expression of another gene or marker. In some embodiments a test agent that increases expression of TRB-3 at least 2-fold relative to an appropriate control is a candidate anti-megakaryocyte agent.

Another embodiment relates to a method of identifying a candidate anti-megakaryocyte agent comprising incubating a cell capable of expressing TRB-3 and a comparison gene (e.g., GpIIb) in the presence of a test agent; measuring expression of TRB-3; and measuring expression of the comparison gene (e.g., GpIIb), wherein a test agent which increases expression of TRB-3 (e.g., by at least about 1.5 fold) without significantly increasing expression of or reducing expression of the comparison gene (e.g., GpIIb) is a candidate anti-megakaryocyte agent. Typically the comparison gene will be a gene whose expression is upregulated during megakaryocyte differentiation, but in certain instances the comparison gene may be a gene whose expression is downregulated during megakaryocyte differentiation. A candidate anti-megakaryocyte agent will increase TRB-3 expression and decrease expression of a gene which is upregulated during megakaryocyte differentiation. Similarly a candidate anti-megakaryocyte agent will decrease TRB-3 expression and increase expression of a gene which is downregulated during megakaryocyte differentiation.

GpIIb is a specific marker of megakaryocyte differentiation; its expression increases during this process. Thus, if GpIIb is used as the comparison gene, a candidate anti-megakaryocyte agent would be expected to decrease expression levels of GpIIb normally found during megakaryocyte differentiation. Accordingly, an anti-megakaryocyte agent would be expected not to significantly increase expression of GpIIb relative to pre-differentiation levels and/or to decrease GpIIb expression relative to levels of GpIIb normally found during megakaryocyte differentiation. Both of these variations are intended to be included herein when reference is made to failure to increase (or lack of increase in) GpIIb expression. In some embodiments the method further comprises determining the ratio of TRB-3 expression to GpIIb expression, wherein a test agent which increases said expression ratio by at least about 2.5-fold is a candidate anti-megakaryocyte agent.

In some embodiments the cell endogenously expresses TRB-3 and/or GpIIb. In some embodiments the cell is a hematopoietic progenitor cell or a megakaryocyte. In some embodiments the cell is a mammalian cell, and in some embodiments the cell is a human cell.

In particular embodiments of the methods described herein more than one cell is incubated with or exposed to the test agent, i.e., populations of cells are incubated with the test agent, such as populations comprising more than 5,000 cells, more than 10,000 cells, more than 15,000 cells, more than 20,000 cells, more than 25,000 cells, more than 30,000 cells, more than 35,000 cells, etc.

In some embodiments the cell or cells are incubated with or exposed to the test agent in advance of or at the beginning of the differentiation period for the megakaryocyte lineage and continued for a period of time (e.g., about 12 hours, 24 hours, 36 hours, 48 hours, 3 days, 4 days, 5 days, etc.). In other embodiments the test agent is added to the cells after differentiation of the megakaryocyte lineage has begun. For example, the test agent can be added about 12 hours, 24 hours, 36 hours, 48 hours, 3 days, 4 days, etc. after differentiation of megakaryocytes has begun, and continued for a period of time (e.g., about 12 hours, 24 hours, 36 hours, 48 hours, 3 days, 4 days, 5 days, etc.). In a particular embodiment the cell or cells are exposed to the test agent beginning on day 3 of the differentiation period and continuing for about 24 hours.

In some embodiments TRB-3 and/or GpIIb expression is measured by measuring a TRB-3 and/or GpIIb expression product. In certain embodiments the expression product is cDNA or mRNA; in other embodiments the expression product is a polypeptide.

In certain embodiments the mRNA expression product is measured using one or more methods selected from the group consisting of polymerase chain reaction, reverse-transcribed polymerase chain reaction, and quantitative polymerase chain reaction. In other embodiments mRNA expression is measured using mass spectrometry. In still other embodiments mRNA expression is measured using one or more microarrays. In some embodiments absolute expression levels are measured, while in other embodiments relative expression levels are measured. For example, TRB-3 expression level may be measured relative to TBP or GUSB expression level (TBP and GUSB expression levels do not change significantly during megakaryocyte differentiation). In some embodiments a test agent which increases expression of TRB-3 at least about 2-fold relative to an appropriate control without significantly increasing or while reducing expression of GpIIb is a candidate anti-megakaryocyte agent.

In some aspects work described herein relates to a method of identifying a candidate agent for inhibiting differentiation of megakaryocytes comprising incubating, in the presence of a test agent, a cell that is capable of expressing TRB-3; and measuring expression of TRB-3, wherein a test agent which increases expression of TRB-3 relative to an appropriate control is a candidate agent for inhibiting differentiation of megakaryocytes. In some embodiments the cell is a hematopoietic progenitor cell.

Other aspects relate to a method of identifying a candidate agent for inhibiting differentiation of megakaryocytes comprising incubating, in the presence of a test agent, a cell that is capable of expressing TRB-3 and GpIIb; measuring expression of TRB-3; and measuring expression of GpIIb, wherein a test agent which increases expression of TRB-3 without significantly increasing expression of GpIIb is a candidate agent for inhibiting differentiation of megakaryocytes. In some embodiments the method further comprises determining the ratio of TRB-3 expression to GpIIb expression, and wherein a test agent which increases said expression ratio by at least about 2.5-fold is a candidate agent for inhibiting differentiation of megakaryocytes. In some embodiments the cell is a hematopoietic progenitor cell.

In some aspects work described herein comprises identifying candidate anti-megakaryocyte agents or candidate agents for inhibiting differentiation of megakaryocytes as described herein and further screening an identified candidate agent for additional properties, including reduced side effects, improved efficacy, improved bioavailability, etc.

Some embodiments also relate to a kit for identifying a candidate anti-megakaryocyte agent comprising: (a) a means for incubating a cell capable of expressing TRB-3 with a test compound; (b) a means for measuring TRB-3 expression. Other embodiments relate to a kit for identifying a candidate anti-megakaryocyte agent comprising: (a) a means for incubating a cell capable of expressing TRB-3 and GpIIb with a test compound; (b) a means for measuring TRB-3 and GpIIb expression. Kits may also optionally comprise means for measuring expression of other comparison or control genes, instructions for use, and/or one or more cells capable of expressing the gene(s) to be measured.

BRIEF DESCRIPTION OF THE DRAWINGS

FIG. 6A shows the effect of anagrelide and indicated compounds on megakaryocyte growth as determined by the conventional megakaryocyte growth assay. FIG. 6B shows the effect of anagrelide or the indicated compounds on TRB-3 or TRB-3/GpIIb expression as determined by the novel TRB-3 expression assay. Cells were cultured and analysed as described in FIGS. 5A-5B.

DETAILED DESCRIPTION OF THE INVENTION

Figure 1:
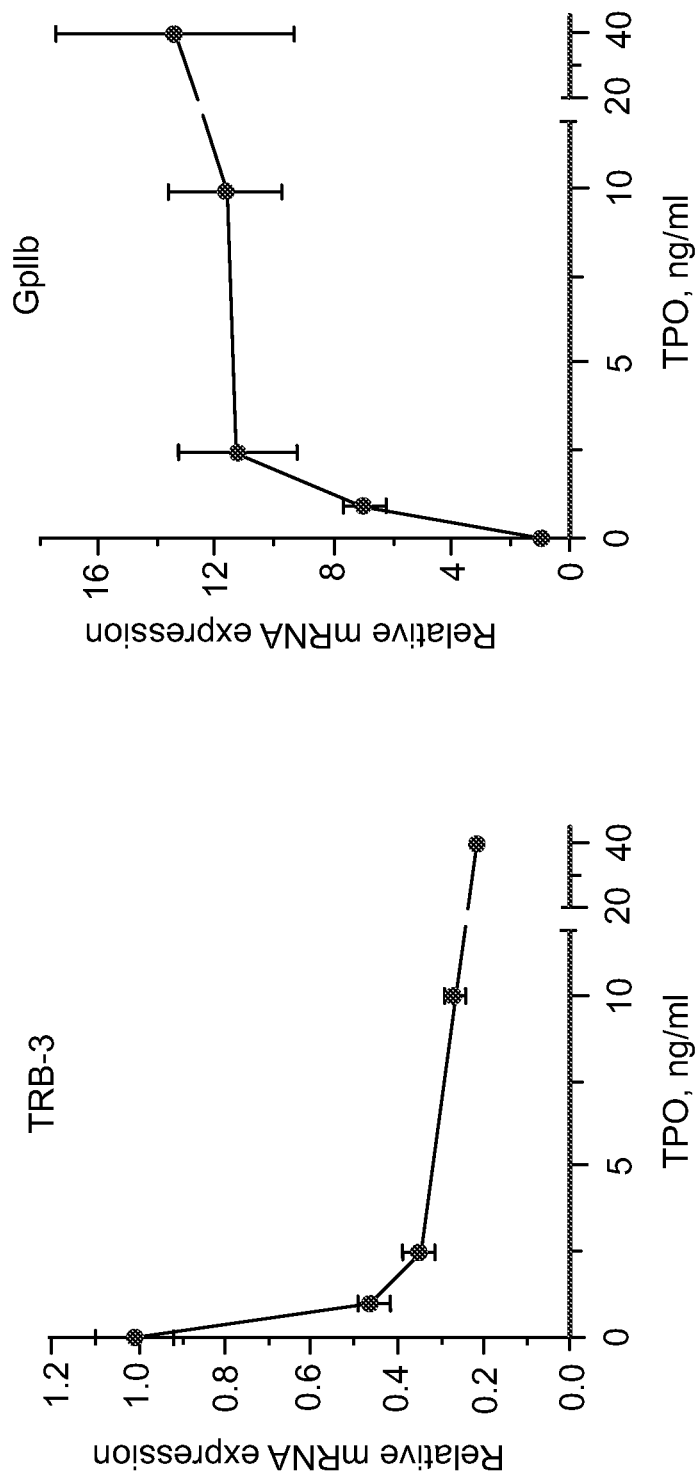
FIG. 1 shows dose-responses for the effect of TPO on TRB-3 and GpIIb mRNA expression. Hematopoietic progenitor cells were grown for four days with the indicated concentrations of TPO under otherwise standard MK culture conditions. TRB-3 and GpIIb mRNA levels were determined by quantitative RT-PCR using GUSB as an endogenous reference. Results (mean±SD of replicate determinations) are expressed relative to the transcript levels detected in the cells at the initiation of the cultures. Error bars (SD) smaller than the size of the symbol are not shown.
Figure 2:
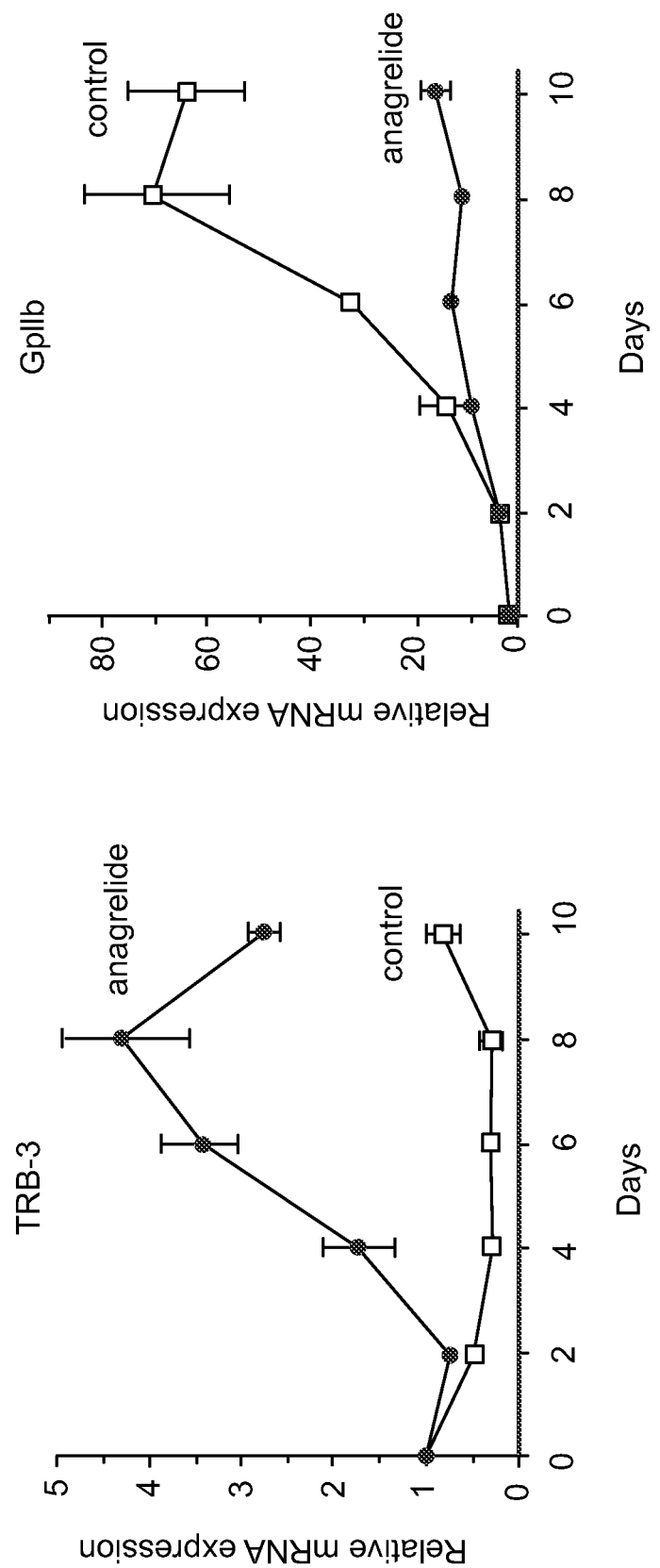
FIG. 2 shows time courses of TRB-3 and GpIIb mRNA expression levels during megakaryocytopoiesis in culture in the absence and presence of 1 µM anagrelide. Hematopoietic progenitor cells were grown for the indicated lengths of time under standard MK culture conditions. Gene expression levels were determined as described in FIG. 1. Error bars (SD) smaller than the size of the symbol are not shown.

The megakaryocyte is a bone marrow cell responsible for the production of blood thrombocytes (platelets), which are necessary for normal blood clotting. Megakaryocytes are derived from hematopoietic stem cells in the bone marrow, which are capable of producing all types of blood cells depending on the differentiation signals they receive. The primary signal for megakaryocyte production is thrombopoietin or TPO; other molecular signals for megakaryocyte differentiation include GM-CSF, IL-3, IL-6, IL-11, the chemokines SDF-1 and FGF-4, and erythropoietin. The megakaryocyte develops from a pluripotent hemopoietic stem cell or hemocytoblast to a megakaryoblast, then to a promegakaryocyte, and finally to a megakaryocyte. Once the cell has completed differentiation and becomes a mature megakaryocyte, it begins the process of producing platelets.

Essential thrombocythemia (ET) is a chronic blood disorder characterized by the overproduction of platelets and megakaryocytes in the bone marrow. The resulting high numbers of platelets circulating in the body can produce thrombosis or clots, as well as, paradoxically, hemorrhagic events. The latter occur because of an acquired Von Willebrand's factor deficiency. The pathologic basis for ET is not completely understood. About 50% of patients with the disease carry a dominant gain of function mutation in the gene JAK2. JAK2 is a non-receptor tyrosine kinase that associates with the receptors for a number of cytokines and growth factors including TPO and erythropoietin, and activates down-stream signal transduction cascades involved in the proliferation and differentiation of hematopoietic cells. The JAK2 mutation renders hematopoietic cells more sensitive to hematopoietic growth factors, resulting in increased myelopoiesis.

Anagrelide is utilized for the treatment of patients with thrombocythemia to reduce the elevated platelet count and to ameliorate associated symptoms such as thrombo-hemorrhagic events. The mechanism by which anagrelide reduces blood platelet count is still under investigation. In vitro culture and patient studies support a hypothesis of dose-related reduction in platelet production resulting from a decrease in megakaryocyte development. However, anagrelide is contraindicated in patients with severe hepatic impairment and should be used with caution in patients with known or suspected heart disease due to the positive inotropic effects emanating from its anti-phosphodiesterase III activity. In addition, a minority of patients are insensitive to or intolerant of the drug. Accordingly it would be beneficial to identify additional agents that can inhibit the proliferation, differentiation or maturation of megakaryocytes and/or reduce elevated platelet count in order to offer improved therapeutic options for some patients.

Thus, in certain aspects the invention relates to methods for identifying candidate agents for inhibiting megakaryocytopoiesis (e.g., inhibiting the proliferation of hematopoietic progenitor cells, inhibiting maturation or differentiation of megakaryocytes, and/or lowering platelet levels). Such agents are referred to herein as anti-megakaryocyte candidate agents or candidate anti-megakaryocyte agents. In certain embodiments candidate anti-megakaryocyte agents may be further screened to identify agents with improved properties when compared with anagrelide, such as reduced side effects, improved bioavailability, and/or improved efficacy. The screening methods of the invention can be carried out manually or in an automated manner.

As described herein, it has been discovered that anagrelide increases TRB-3 expression, and that TPO decreases TRB-3 expression. TRB-3 (also known as TRIB3, tribbles-related protein 3, or *homo sapiens* tribbles homologue 3 (Drosophila) encodes a pseudokinase, and in certain cell types its expression is regulated during stress response and change of nutrient status. The TRB-3 gene (Entrez gene ID #57761) was originally cloned from a human hepatoma cell line and is identical to human SKIP3 (GenBank accession #AF0250311). Du et al. identified the TRB-3 protein as a novel Akt-binding and -regulating protein (Du et al., Science 300:1574-1577 (2003)). TRB-3 modulates the activity of several signal transduction cascades, including Akt protein kinases, the ATF4 and CHOP transcription factors, and the NF-κB pathway. Expression of TRB-3 can be utilized as described herein to identify or assist in the identification of candidate anti-megakaryocyte agents, either alone or in combination with other screening methods.

In one aspect the invention relates to a method of identifying or screening for a candidate anti-megakaryocyte agent comprising incubating a cell that expresses TRB-3 in the presence of a test agent; and measuring expression of TRB-3, wherein a test agent that increases expression of TRB-3 relative to an appropriate control is a candidate anti-megakaryocyte agent. In other embodiments the invention relates to incubating TRB-3-expressing cells in the presence or absence of one or more test drugs, compounds or other therapeutic agents (test agents), followed by the step of measuring the level of induced TRB-3 expression attributable to administration of the test agent(s) and selecting test agents capable of inducing or increasing expression of TRB-3 relative to a control compound. Candidate anti-megakaryocyte agents may be, for example, direct TRB-3 agonists (i.e., agents which have a direct agonistic effect on TRB-3 itself, increasing or inducing TRB-3 expression) or TRB-3 pathway agonists (i.e., agents which have an agonistic effect on the pathway leading to (upstream of) TRB-3 expression such that TRB-3 expression is increased or induced). The invention also relates, in one embodiment, to a method of screening for compounds which modulate (i.e. increase or decrease) TRB-3 expression.

In most embodiments, cells suitable for use in the invention are cells capable of expressing TRB-3, such as cells which are capable of expressing TRB-3 in the absence of test agent. In certain embodiments suitable cells endogenously express TRB-3, while in other embodiments the cells have been engineered to express TRB-3 using methods known in the art. Cells suitable for use in the invention may be obtained from a biological sample. As used herein, a biological sample is any sample obtained from an organism, including body fluids, cell lines, tissue culture, and other cell sources. Cells may be, for example, mammalian cells, including, without limitations, primate, e.g., human, cells. Useful cells include, but are not limited to, hematopoetic progenitor cells, megakaryoblasts, promegakaryocytes, and megakaryocytes.

In another embodiment of the invention, candidate agents can be identified using a cell, cell lysate, or solution containing a nucleic acid encoding the promoter region of TRB-3 operably linked to a reporter gene. As used herein "promoter" means a minimal nucleotide sequence sufficient to direct transcription, and "operably linked" means that a gene and one or more regulatory sequences are connected in such a way as to permit gene expression when the appropriate molecules (e.g., transcriptional activator proteins) are bound to the regulatory sequences. Examples of reporter genes and methods for operably linking a reporter gene to a promoter are known in the art. After contact with a test agent, the level of expression of the reporter gene (e.g., the level of mRNA or of protein expressed) is assessed, and is compared with the level of expression in a control (i.e., the level of expression of the reporter gene in the absence of the test agent, or in the presence of the test agent vehicle only). If the level of reporter gene expression in the presence of the test agent differs by an amount or in a manner that is statistically significant from the level in the absence of the test agent, or in the presence of the test agent vehicle only, then the test agent is a candidate anti-megakaryocytic agent.

In another embodiment, the level of expression of the reporter in the presence of the test agent, is compared with a control level that has been established previously. A level in the presence of the test agent that differs from the control level by an amount or in a manner that is statistically significant indicates that the test agent is a candidate anti-megakaryocyte agent.

Test agents may be selected from among known therapeutic agents (i.e., agents with known therapeutic efficacy) or agents with previously unknown therapeutic activity. Test agents include, without limitation, chemical molecules, be it naturally-occurring or artificially-derived, and includes, for example, peptides, proteins, synthesized molecules, for example, synthetic organic molecules, naturally-occurring molecules, for example, naturally occurring organic molecules, nucleic acid molecules, and components thereof. Test agents may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. A plurality of assay mixtures may be run in parallel with different agent concentrations to obtain a differential response to the various concentrations. Typically one of these concentrations serves as a negative control, i.e., at zero concentration or below the level of detection. One or more test agents can be incubated with an appropriate cell. For example, combinations of agents can be tested to identify potential combinatorial therapies.

When a crude extract is found to induce or increase TRB-3 expression, further fractionation of the positive lead extract may be performed to isolate chemical constituents responsible for the observed effect. Thus, the goal of the extraction, fractionation, and purification process is the careful characterization and identification of a chemical entity within the crude extract having an activity that induces or increases TRB-3 expression. The same assays described herein for the detection of TRB-3-inducing-activity in mixtures of agents can be used to purify the active component and to test derivatives thereof. Methods of fractionation and purification of such heterogenous extracts are known in the art. If desired, compounds shown to be useful agents for treatment can be chemically modified according to methods known in the art. Compounds identified as being candidate agents of potential therapeutic value may be subsequently analyzed using other procedures, including animal models.

One or more test agents and one or more appropriate cells are incubated together for a period of time and under conditions sufficient for expression of TRB-3. Incubations may be performed at any suitable temperature, typically between 4 and 40° C., and for a suitable length of time. Incubation conditions will depend on the type of cell utilized and are known to the skilled artisan. For example, conventional growth conditions for megakaryocyte cultures are well known in the art. Incubation periods are selected for optimum activity, but may also be optimized to facilitate rapid high-throughput screening.

In some embodiments the cell or cells are incubated with or exposed to the test agent in advance of or at the beginning of the differentiation period for the megakaryocyte lineage and continued for a period of time (e.g., about 12 hours, 24 hours, 36 hours, 48 hours, 3 days, 4 days, 5 days, etc.). In other embodiments the test agent is added to the cells after differentiation of the megakaryocyte lineage has begun. For example, the test agent can be added about 12 hours, 24 hours, 36 hours, 48 hours, 3 days, 4 days, etc. after differentiation of megakaryocytes has begun, and continued-for a period of time (e.g., about 12 hours, 24 hours, 36 hours, 48 hours, 3 days, 4 days, 5 days, etc.).

In a particular embodiment the cell or cells are exposed to the test agent beginning on day 3 of the differentiation period and continuing for about 24 hours. As described herein, higher increases in TRB-3 expression can be obtained under these conditions, revealing a 24 hour time window (between day 3 and day 4) in which the sensitivity of the assay is increased. Moreover, shorter incubation time allows for the testing of compounds that may be less stable in aqueous media.

After a suitable incubation period, TRB-3 expression is measured. Measurement of TRB-3 expression encompasses qualitatively or quantitatively measuring or estimating the level of a TRB-3 expression product either directly (e.g., by determining or estimating absolute expression product level) or relatively (e.g., by comparing to the expression product level in a second cell or population of cells or relative to the expression product level of one or more other markers in the same cell or population of cells). For example, a control standard may be determined (e.g., TRB-3 expression level in the same cell type in the absence of the test agent) once and then used repeatedly as a standard or control for comparison.

In certain embodiments the TRB-3 expression product which is measured is TRB-3 cDNA or mRNA which can be measured by many methods known in the art. For example, the invention encompasses the application of PCR methodology. PCR techniques for the amplification of nucleic acids are described, for example, in U.S. Pat. No. 4,683,195 and Saiki et al., *Science* 239:487-491 (1988). PCR, for example, may include the steps of denaturation of template nucleic acid (if double-stranded), annealing of primer to target, and polymerization. The nucleic acid probed or used as a template in the amplification reaction may be cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., *Cold Spring Harbor Symp. Quant. Biol.* 51:263, (1987); Ehrlich (ed), PCR Technology, Stockton Press, NY, 1989; Ehrlich et al., *Science* 252:1643-1650, (1991); and "PCR Protocols, A Guide to Methods and Applications", Eds., Innis et al., Academic Press, New York, (1990). For example, TRB-3 mRNA may be measured using standard PCR, reverse-transcription PCR(RT-PCR) or quantitative real time PCR.

The present invention also encompasses the use of microarrays, e.g., nucleotide microarrays, which can be used in conjunction with the disclosed screening assays for measuring TRB-3 expression. These microarrays can be used in the manual or automated screening assays of the invention as disclosed herein to test one or more test agents. In one embodiment a nucleic acid sample (e.g., mRNA) is contacted with a suitable microarray on which probes specific for the mRNA have been immobilized (alone or in combination with probes specific for other polynucleotide sequences), and determining the extent of hybridization of the nucleic acid in the sample to the probes on the microarray. Microarrays having immobilized thereon probes specific for TRB-3 (and/or GPIIb) are also within the scope of the invention. Examples of methods of making oligonucleotide microarrays are described, for example, in WO 95/11995. Other methods are readily known to the skilled artisan.

In the context of nucleotide microarrays, gene expression values are typically raw values obtained from an apparatus that reads the array, or values that are optionally rescaled, filtered and/or normalized. Such data can be obtained, for example, from a GeneChip® probe array (Affymetrix, Inc.) (U.S. Pat. Nos. 5,631,734, 5,874,219, 5,861,242, 5,858,659, 5,856,174, 5,843,655, 5,837,832, 5,834,758, 5,770,722, 5,770,456, 5,733,729, 5,556,752, all of which are incorporated herein by reference in their entirety), and the expression levels can be calculated with software (e.g., Affymetrix GENECHIP® software). The nucleic acid to be analyzed (e.g., the target) is isolated, amplified and labeled with a detectable label (e.g., $^{32}$P or fluorescent label) prior to hybridization to the arrays. Once hybridization occurs, the arrays are inserted into a scanner which can detect patterns of hybridization. The hybridization data are collected as label (e.g., light, radioactive signal, etc.) emitted from the labeled groups which are now bound to the probe array. The probes that perfectly match the target produce a stronger signal than those that have mismatches. Since the sequence and position of each probe on the array are known, by complementarity, the identity of the target nucleic acid applied to the probe is determined.

Quantitation of gene profiles from the hybridization of labeled mRNA/DNA microarrays can be performed by scanning the microarrays to measure the amount of hybridization at each position on the microarray with an Affymetrix scanner (Affymetrix, Santa Clara, Calif.).

Other methods for obtaining gene expression values known in the art or developed in the future can also be used with the present invention, such as mass spectrometry.

In other embodiments the TRB-3 expression product which is measured can be a TRB-3 polypeptide. As used herein a TRB-3 polypeptide is a polypeptide comprising all or an identifying portion of the full length amino acid sequence of TRB-3. TRB-3 polypeptide can be detected by a variety of methods known in the art, including antibody technologies, binding assays, and the like.

The present invention also encompasses the use of microarrays, e.g., protein, antibody, or cell-based microarrays, which can be used in conjunction with the disclosed screening assays for measuring TRB-3 polypeptide levels. For protein microarrays, polypeptides obtained from one or more cells (e.g., from extracellular media or cell lysates) incubated in the presence and/or absence of at least one test agent can be affixed to a support, and then contacted with antibodies that specifically bind to the TRB-3 polypeptide. For antibody microarrays, one or more anti-TRB-3 antibodies can be affixed to a support, and then contacted with extracellular media or cell lysates obtained from one or more cells incubated in the presence and/or absence of at least one test agent. For cell-based microarrays, one or more cells can be affixed to a support, and then incubated in the presence and/or absence of at least one test agent. The microarrays can then be analyzed (e.g., by immunoassay) to determine levels of TRB-3 polypeptide.

Publications setting forth useful proteomics methodologies include the following: McDonald W H, Yates J R 3rd., *Dis. Markers.* 18(2):99-105 (2002); Link A J, *Trends Biotechnol.* December 20(12 Suppl):S8-13 (2002); Gao et al., *Toxicology In Vitro* 18(4): 533-541 (2004); Gao et al., *Journal of Proteome Research* 2(6):643-649 (2003); and Pang et al., *Journal of Proteome Research* (2):161-169 (2002).

According to embodiments of the methods of the invention, TRB-3 expression levels determined from cells incubated with test agents are analyzed to identify increases caused by the test agent. For example, expression levels can be contained with an appropriate control, such as TRB-3 expression in a similar cell in the absence of the test agent. Preferred anti-megakaryocyte agents will increase TRB-3 expression by at least 1.5-fold (e.g., 1.5-fold, 2-fold, 2.5-fold, 3-fold, 3.5-fold, 4-fold, 5-fold or greater, etc.). Alternatively, preferred anti-megakaryocyte agents will increase the ratio of TRB-3/GpIIb expression by greater than 1.5-fold, greater than 2-fold, greater than 2.5-fold, greater than 3-fold, etc.

It should be noted that although the primary focus of the subject screening methods is to identify agents which increase or induce TRB-3 expression, the assays will also identify agents which decrease TRB-3 expression. Characterization of agents as decreasing TRB-3 expression has value in contexts outside of identifying anti-megakaryocyte agents. For example, as shown herein, TPO reduces TRB-3 expression; thus decreased TRB-3 expression may be used to detect TPO mimetics or agonists.

The robustness and sensitivity of the readout of the screening assays described herein with regard to TRB-3 may be improved by combining measurement of TRB-3 expression with expression of an additional gene whose expression is increased or is induced during megakaryocyte development (such as GpIIb); the ratio of TRB-3 expression to expression of the additional gene may be calculated and used to identify candidate anti-megakaryocyte agents. All disclosure contained herein with regard to suitable test agents and cells, and measurement of expression with regard to TRB-3 is equally applicable and relevant to expression of other genes such as GpIIb, TBP and GUSB. This disclosure is not repeated here specifically substituting, e.g., "GpIIb" for "TRB-3," but inclusion of this disclosure is understood.

The validity of this approach is confirmed in the examples disclosed herein below and allows assessment of TRB-3 expression on smaller populations of cells than when TRB-3 expression alone is used as the readout. GpIIb (platelet glycoprotein IIb of IIb/IIIa complex, Entrez gene ID #3674; also known as integrin alpha 2b, antigen CD41 and ITGA2B) encodes the alpha chain of integrin alpha 2b/beta 3 found on megakaryocytes and platelets. GpIIb associates with GpIIIa (also known as beta 3) to form a receptor for fibrinogen, von Willebrand factor and fibronectin. Binding to soluble fibrinogen mediates normal platelet aggregation.

In some embodiments candidate anti-megakaryocyte agents will preferentially increase TRB-3 expression but not significantly (e.g., statistically significantly) increase GpIIb expression from baseline levels or will reduce GpIIb expression from the levels typically associated with megakaryocyte differentiation. In other embodiments a ratio of TRB-3 expression to GpIIb expression is determined, and in preferred embodiments candidate anti-megakaryocyte agents increase this ratio by 2-fold, 2.5-fold or greater (e.g., 3-fold, 3.5-fold, 4-fold, 5-fold or greater, etc.).

Also included herein are kits for identifying a candidate anti-megakaryocyte agent comprising: (a) a means for incubating a cell that expresses TRB-3 (and, optionally, GpIIb) with a test compound; (b) a means for measuring TRB-3 expression. The kits may further comprise a means for measuring GpIIb expression. Kits may further comprise adjunct elements (e.g., buffers, instruments, instructions, test compounds, etc.)

Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. It is contemplated that all embodiments described herein are applicable to all different aspects of the invention. It is also contemplated that any of the embodiments can be freely combined with one or more other such embodiments whenever appropriate. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more elements or limitations found in any other claim that is dependent on the same base claim, and any claim that refers to an element present in a different claim can be modified to include one or more elements or limitations found in any other claim that is dependent on the same base claim as such claim. Furthermore, where the claims recite a composition, the invention provides methods of making the composition, e.g., according to methods disclosed herein, and methods of using the composition, e.g., for purposes disclosed herein. Where the claims recite a method, the invention provides compositions suitable for performing the method, and methods of making the composition. Also, where the claims recite a method of making a composition, the invention provides compositions made according to the inventive methods and methods of using the composition, unless otherwise indicated or unless one of ordinary skill in the art would recognize that a contradiction or inconsistency would arise.

Where elements are presented as lists, e.g., in Markush group format, each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and, that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

In addition, any particular embodiment(s), aspect(s), element(s), feature(s), etc., described herein, e.g., any compound, cell type, condition, disease, etc., may be explicitly excluded.

The invention will be further illustrated by the following non-limiting examples. The teachings of all references cited herein are incorporated by reference.

EXAMPLES

Example 1

Materials & Methods

Drugs

Anagrelide hydrochloride hydrate was supplied by Cambridge Major Laboratories (Batch No CML-217/03-RS6; Lot 70621) in DMSO. Other test agents were synthesised and supplied by NewChem Technologies Ltd (Durham, UK). Stock solutions (2 mM) were made in DMSO and stored at −20° C. in small aliquots until required. Compounds were diluted in culture medium immediately before addition to cell suspensions.

CD34+ Cells

Cryo-preserved CD34+ haematopoietic progenitor cells were purchased from Stem Cell Technologies (London, UK) and stored in liquid nitrogen until use.

Expansion of Haematopoietic Progenitor Cells

CD34+ cells were thawed, washed by centrifugation (300 g for 10 min at room temperature) in Stemspan™ medium (Stem Cell Technologies, London, UK) and then seeded in 48-well Falcon plates at a density of $1.5 \times 10^5$ cells/ml in the above culture medium supplemented with 100 U/ml penicillin, 0.1 mg/ml streptomycin, 0.25 µg/ml amphothericin B, 2% human umbilical cord blood plasma, 40 ng/ml TPO (Insight, UK), 50 ng/ml SCF, 100 ng/ml Flt3 ligand, and 10 ng/ml IL-3 (all from R&D Systems, Abingdon, UK). Cells were grown four days at 37° C. in a humidified incubator under 5% $CO_2$/95% air.

Standard Megakaryocyte Culture

The expanded cells were washed free of cytokines by centrifugation as above and re-suspended to $1.5 \times 10^5$ cells/ml by addition of fresh Stemspan™ culture medium containing 2% human umbilical cord plasma and 40 ng/ml TPO. Cells were then grown in 48-well Falcon plates at 37° C. in a humidified incubator under 5% $CO_2$/95% air in the presence of either anagrelide, another test agent or an equivalent amount of vehicle (between 0.01% to 0.05% DMSO). At various time points the cells were harvested and processed for RNA extraction or for determination of CD61 antigen expression and total cell counting.

Cell Counting and Analysis of Megakaryocytic Lineage Differentiation (Conventional Megakaryocyte Growth Assay)

The final cell density of the cultures was determined using a Casy TT Cell counter (Innovatis, Germany) set with a lower cut-off limit of ~8 µmeter. Megakaryocytic differentiation was monitored by flow cytometry using the FITC-conjugated monoclonal antibodies: Y2/51 (Dako Cytomation, UK), which detects the megakaryocytic lineage specific marker CD61 (glycoprotein IIIa). Cells were stained and then fixed in 0.5% paraformaldehyde prior to analysis in a Coulter Epics XL™ flow cytometer (Beckman Coulter). The fraction of antigen positive cells was established according to the fluorescence distribution of cells stained with an isotype-matched control antibody. The number of megakaryocytic cells was calculated by multiplying the total number of cells in the culture by the fraction of CD61 positive cells.

RNA Expression Analysis by Quantitative RT-PCR (TRB-3 Expression Assay)

Cellular RNA was extracted with RNeasy reagent (Qiagen) according to the manufacturer's instructions and cDNA was prepared from 0.1-0.5 µg total RNA template using random hexamer primers and a High Capacity Reverse Transcription kit or a High Capacity RNA-to-cDNA Master Mix (Applied Biosystems). cDNA aliquots were either used immediately or stored at −20° C. for PCR analysis at a later stage. cDNA aliquots (equivalent to 5-10 ng of input RNA) were then analysed in duplicates by real-time PCR using gene-specific TaqMan probes on an ABI Prism 7500 Sequence Detection System (Applied Biosystems). Probes for TRB-3 (Hs00221754_m1), GpIIb (Hs00166246_m1), GUSB (Hs99999908_m1) and TBP (Hs99999910_m1) were commercially available from the Assay on Demand gene expression collection (Applied Biosystems). Thermal conditions were the following: 20 seconds at 95° C. followed by 40 cycles of 3 seconds at 94° C. and 30 seconds at 60° C. Reactions without cDNA were included as controls. Relative mRNA expression levels were calculated using the comparative cycle threshold ($C_T$) method (Livak and Schmittgen, 2001) using the $C_T$ values obtained for β-glucuronidase (GUSB) or TATA Box binding protein (TBP) as internal references. For each target gene to be quantified, validation experiments were performed to determine that the efficiency of amplification of target and reference gene was approximately equal. When analysing dose responses $EC_{50}$ values were calculated with Prism software (Version 4, GraphPad Software Inc, CA, USA).

Results

TRB-3 Expression Screen

In order to ascertain the sensitivity of the described method, dose-response curves were constructed based on the effect of anagrelide on TRB-3 mRNA expression using different numbers of cells. Cells were cultured for 4 days under standard MK culture conditions in the presence of increasing concentrations of anagrelide. RNA was extracted from the cells, and TRB-3 mRNA expression was determined by quantitative RT-PCR using β-glucuronidase as an endogenous reference. Results shown in FIG. 3 were expressed relative to the TRB-3 mRNA level detected in cells treated with vehicle alone. $EC_{50}$ values were calculated using a sigmoidal dose response (variable slope) curve-fit model. Values in brackets represent the 95% CI. Error bars (SD) smaller than the size of the symbol are not shown.

Figure 3:
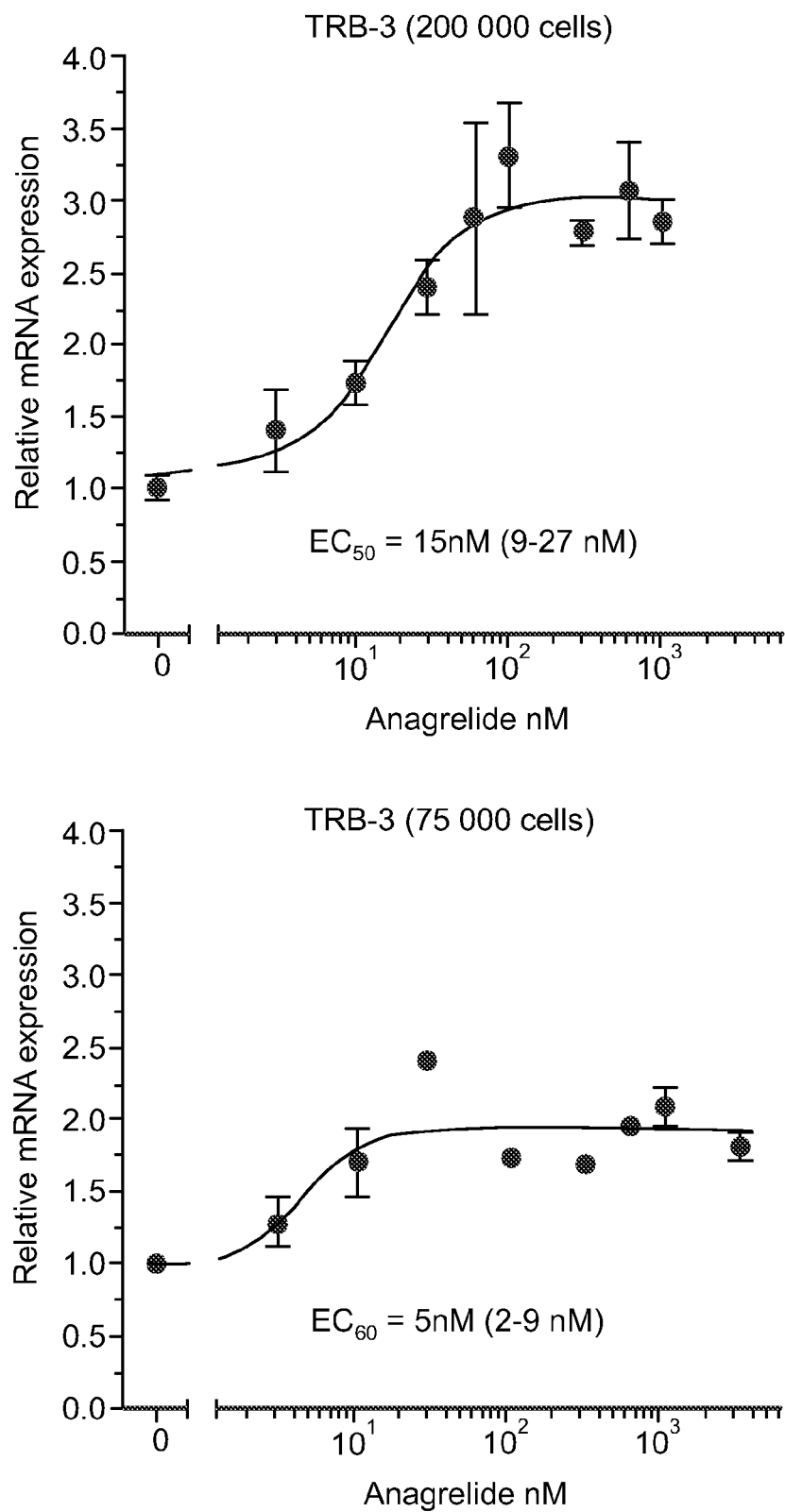
FIG. 3 illustrates dose-responses for the effect of anagrelide on TRB-3 mRNA expression. Hematopoietic progenitor cells were grown for 4 days with the indicated concentrations of anagrelide under standard MK culture conditions. RNA was extracted from the indicated number of cells. Gene expression levels were determined as described in FIG. 1 except that values (mean±SD of replicate determinations) are expressed relative to the transcript levels detected in the cells treated with vehicle alone. Values in brackets represent the 95% CI of the $EC_{50}$. Error bars (SD) smaller than the size of the symbol are not shown
Figure 3:
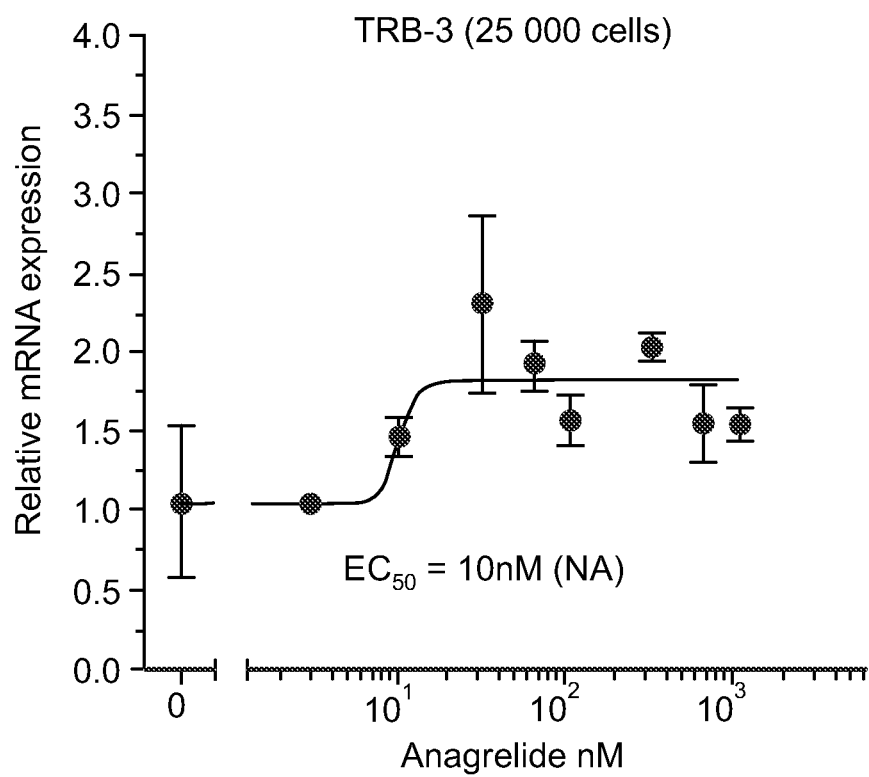

FIG. 3 shows that a clear dose-dependent increase in the expression of TRB-3 was only observed when the RNA extraction step was performed with 200,000 cells. In this case the calculated $EC_{50}$ is 15 nM (95% CI=9 to 27 nM). When the number of cells in the RNA extraction step was reduced, there was a decrease in the dynamic range of the assay. This resulted in an apparent decrease in the extent of the response from a 3-fold increase with 200,000 cells to 1.8-fold with 25,000 cells. These results suggest that the abundance of the TRB-3 transcript in the cellular RNA pool is low, and, hence, a larger number of cells is required to improve the signal to noise ratio of the assay. Attempts to improve the dynamic range of the assay with 25,000 cells by introducing a cDNA pre-amplification step prior to PCR were unsuccessful.

TRB-3/GpIIb Expression Screen

Figure 4:
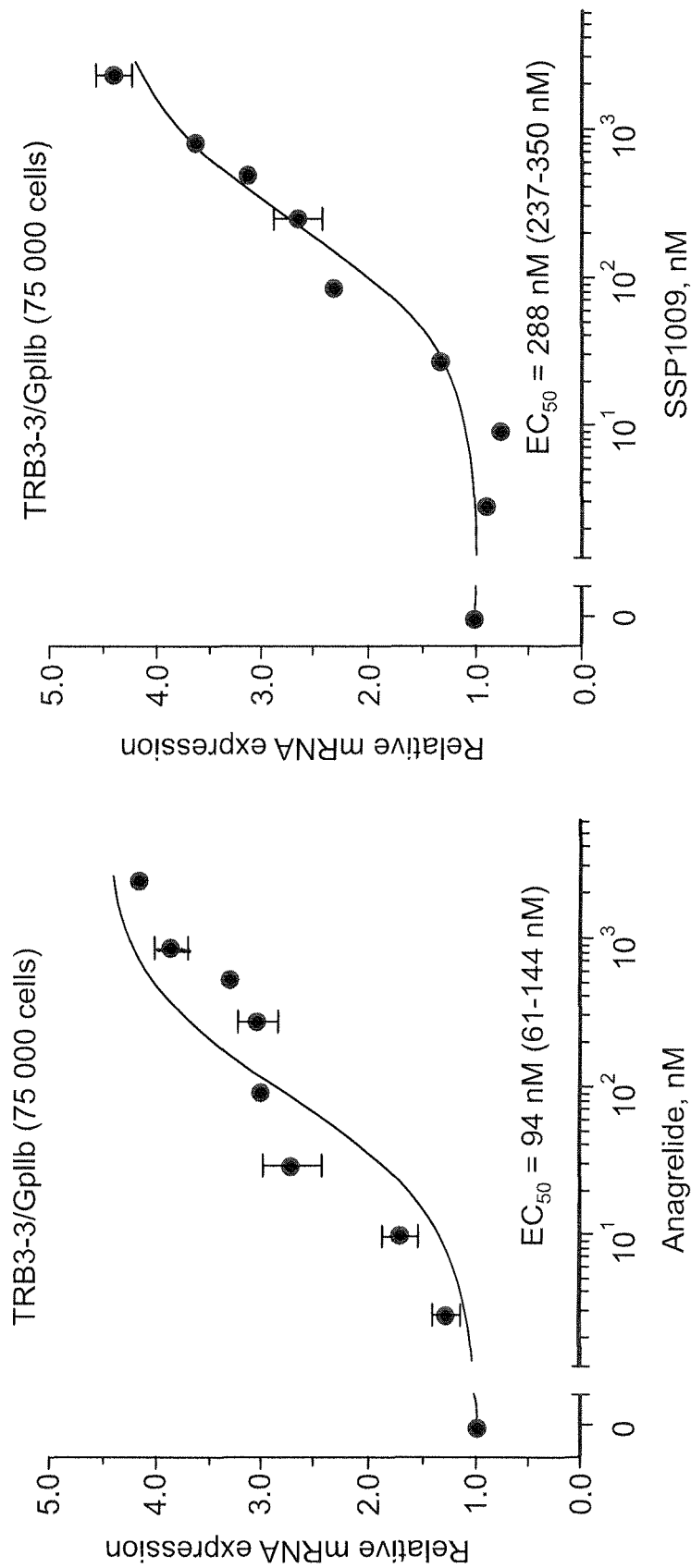
FIG. 4 shows dose-responses for the effect of anagrelide and SSP1009 on TRB-3/GpIIb mRNA expression. Hematopoietic progenitor cells were cultured as described in FIG. 3 with the indicated concentrations of anagrelide or SSP1009. RNA was extracted from 75000 cells. Gene expression levels were measured as described in FIG. 3. Values in brackets represent the 95% CI of the $EC_{50}$. Error bars (SD) smaller than the size of the symbol are not shown.

In view of the ease with which PCR-based assays can be used to evaluate multiple transcripts, further investigation was conducted to determine whether the sensitivity of the assay could be improved by using the ratio of TRB-3/GpIIb mRNA expression as the readout. Cells were cultured for 4 days under standard MK culture conditions in the presence of increasing concentrations of anagrelide or SSP1009 (an anti-megakaryocyte agent), and RNA was extracted from 75,000 cells. TRB-3 and GpIIb mRNA levels were determined by quantitative RT-PCR using β-glucuronidase as an endogenous reference. Results shown in FIG. 4 are expressed relative to the transcript levels detected in cells treated with vehicle alone. $EC_{50}$ values were calculated using a sigmoidal dose-response curve-fit model and fixing the bottom and top parameters to 1-fold and 4.5-fold, respectively (this assumes that the maximal achievable effect is the same with both compounds). Values in brackets represent the 95% CI. Error bars (SD) smaller than the size of the symbol are not shown.

As shown in FIG. 4, this approach enabled the construction of dose-responses bearing a higher dynamic range using 75,000 cells, as well as a comparison between the potencies of anagrelide and SSP1009.

Evaluation of Candidate Agents

Figure 5A:
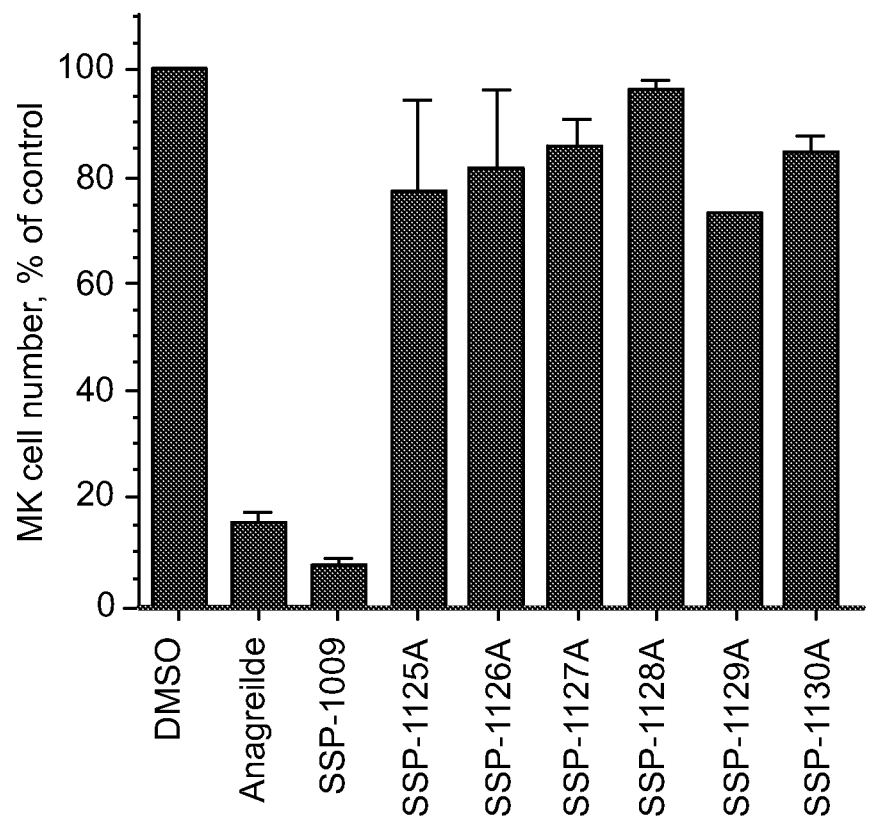
FIGS. 5A and 5B illustrate the screening of selected anagrelide analogues for anti-megakaryocyte activity using the conventional megakaryocyte growth assay (FIG. 5A) and the novel TRB-3 expression assay (FIG. 5B). Cells were cultured for one week (FIG. 5A) or for 4 days (FIG. 5B) in the presence of anagrelide or the indicated compounds (1.0 µM) under standard MK culture conditions. For the megakaryocyte growth assay cells were counted, analyzed by flow cytometry and results (mean±SD of 2 replicates) expressed relative to number of megakaryocytes obtained in the presence of the drug vehicle alone. For the TRB-3 expression assay, transcript levels were determined by quantitative RT-PCR using GUSB as an endogenous reference. Results (mean±SD of replicate determinations) are expressed relative to the transcript levels detected in cells treated with vehicle alone.
Figure 5B:
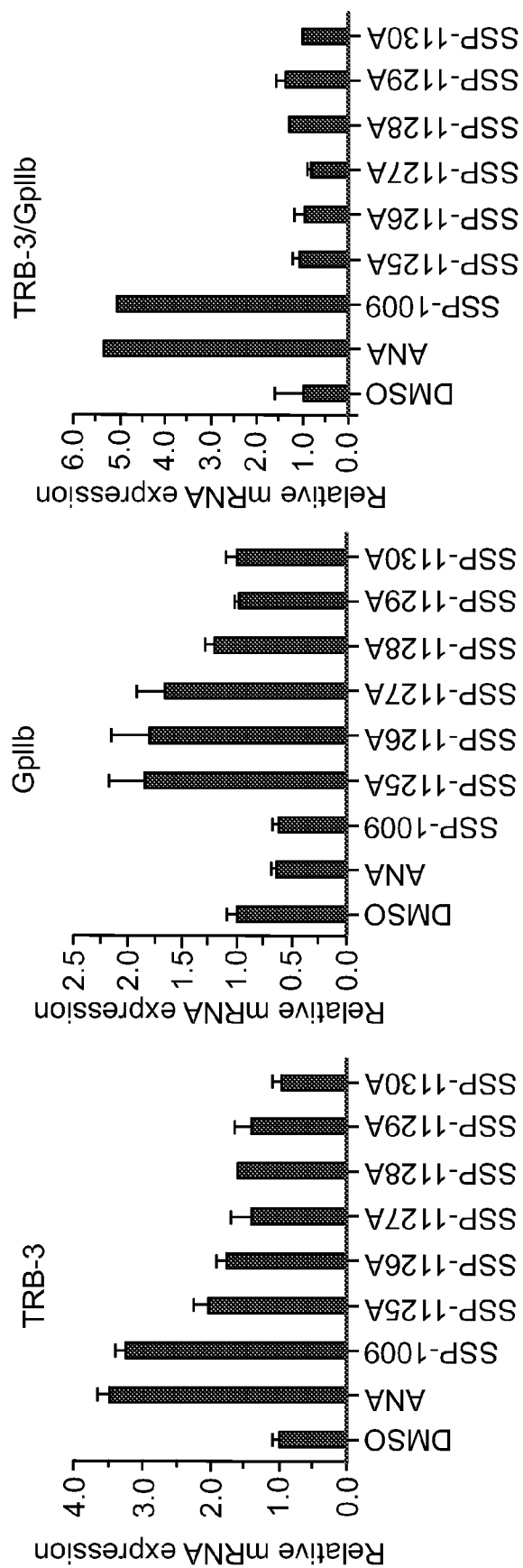

An additional six agents (SSP-1125A, SSP11126A, SSP-1127A, SSP-1128A, SSP-1129A, and SSP1130A) were evaluated for anti-megakaryocyte activity. For the MK growth assay, cells were cultured for one week in the presence of anagrelide or the indicated compounds (1.0 µM) under standard MK culture conditions and then analyzed by flow cytometry. Results (mean±SD of 2 replicates) shown in FIG. 5A are expressed relative to number of megakaryocytes obtained in the presence of the drug vehicle alone. For the TRB-3 expression assay, cells were incubated with the indicated compounds for 4 days as described above. TRB-3 and GpIIb mRNA levels were determined by quantitative RT-PCR using β-glucuronidase as an endogenous reference. Results shown in FIG. 5B are expressed relative to the transcript levels detected in cells treated with vehicle alone.

Compared to anagrelide or SSP1009, none of the additional compounds had significant activity when tested at a concentration of 1 µM under the conventional MK growth assay. Lack of activity was confirmed when the compounds were tested by the TRB-3-based assay using the TRB-3/GpIIb ratio readout.

In addition, three new compounds (SSP-1003X, SSP-1158X, and SSP-1162B) were assessed using both the conventional MK growth assay and the TRB-3-based assay. For the MK growth assay cells were grown for one week in the presence of anagrelide or the indicated compounds (1.0 µM) under standard MK culture conditions and then analyzed by flow cytometry. Results shown in FIG. 5A are expressed relative to controls incubated in the presence of the drug vehicle alone. For the TRB-3 expression assay, cells were cultured for four days as described for FIG. 5B and then TRB-3 and GpIIb mRNA levels were determined by quantitative RT-PCR using β-glucuronidase as an endogenous reference. Results shown in FIG. 5B are expressed relative to the transcript levels detected in cells treated with vehicle alone.

Figure 6A:
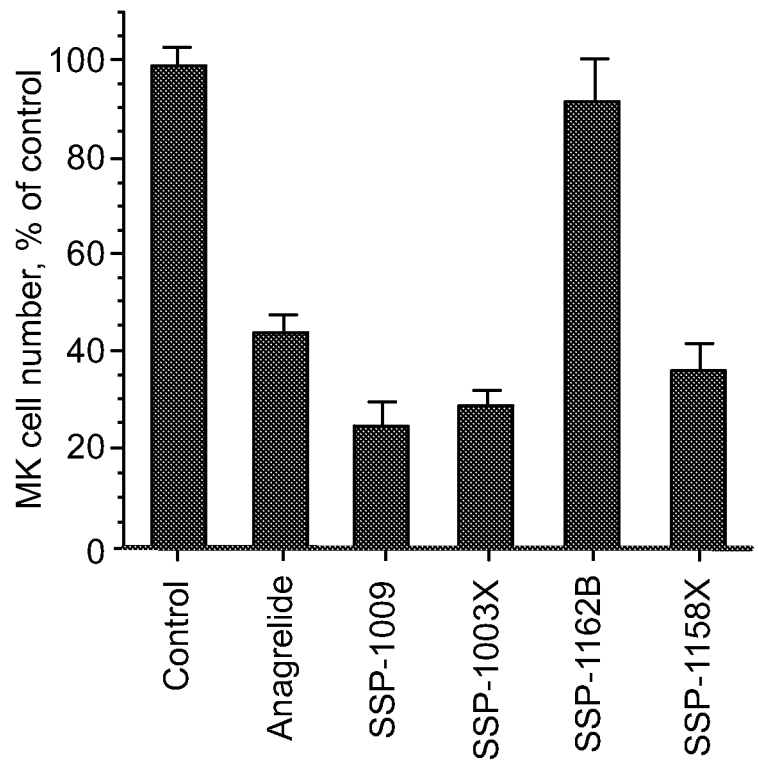
FIGS. 6A and 6B illustrate the screening of additional anagrelide analogues for anti-megakaryocyte activity.
Figure 6B:
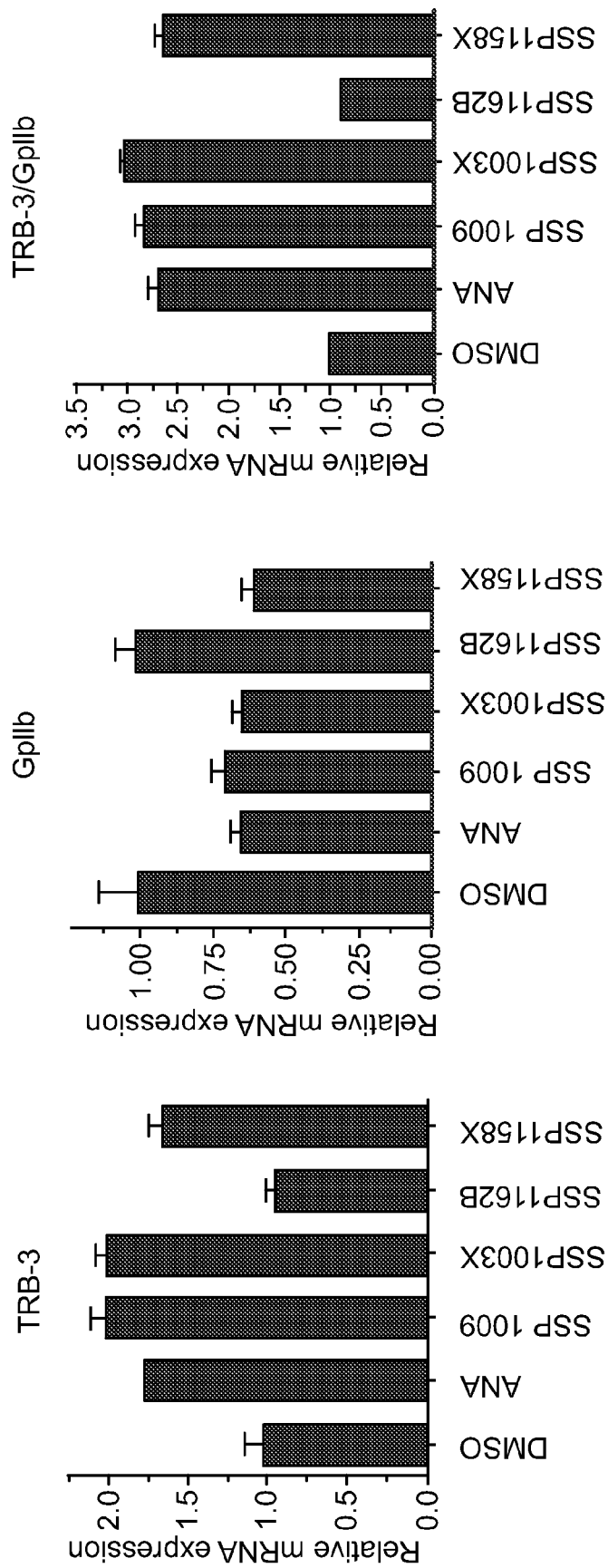

SSP-1162B showed no activity when tested under the conventional MK growth assay, whereas SSP-1003X and SSP-1158X showed activity comparable to anagrelide and SSP1009 (FIG. 6A). The same activity profile was reproduced when these compounds were tested in the TRB-3 expression assay using either TRB-3 mRNA expression alone as the readout or the combined and more sensitive TRB-3/GpIIb readout (FIG. 6B).

These results validate the reliability of TRB-3 expression-based assay methods for screening for candidate anti-megakaryocyte agents.

Example 2

Previous studies have underscored the selectivity of anagrelide for the megakaryocyte lineage (Wang et al., *Brit. J. Pharmacol.* 146: 324-332 (2005)). One possibility to explain this behavior of the drug is that its target is a molecule which is induced exclusively during the differentiation of this lineage. If this were the case the increase in TRB-3 mRNA expression induced by anagrelide would be maximized by adding the drug after the process of differentiation had already started. Work described below examined the levels of expression of TRB-3 mRNA following a short window of exposure to the drug during various time points of the differentiation process.

Materials and Methods

Expanded CD34+ cells (see Materials and Methods Section of Example 1) were pre-incubated for various lengths of time under standard megakaryocyte culture conditions in the absence of the test agent and then treated with the test agent or an equivalent amount of vehicle for 24 hours prior to harvesting. TRB-3 mRNA expression was determined as described in the Materials and Methods Section of Example 1.

Results

Figure 7:
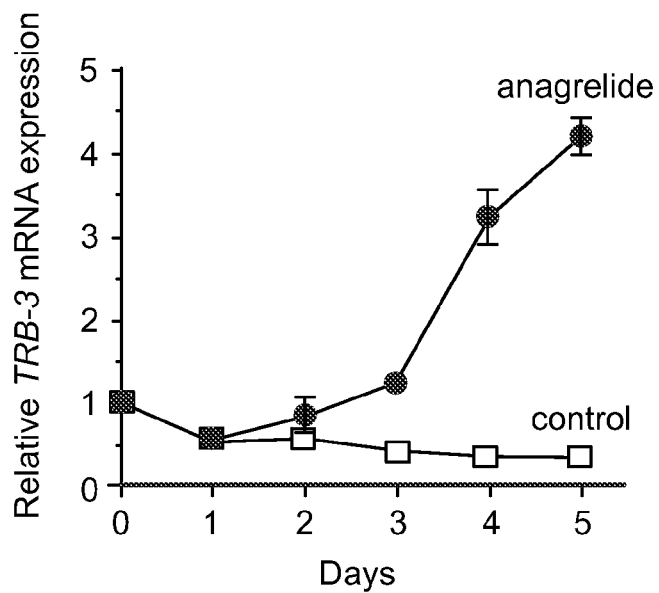
FIG. 7 shows a time course for the effect of anagrelide on TRB-3 mRNA expression when the drug was added for a fixed period of time (24 h), starting at various points after the initiation of the culture. Expanded CD34+ cells were cultured with TPO under standard megakaryocyte culture conditions for the indicated lengths of time. Anagrelide (1 µM) or an equivalent amount of vehicle (control) were added 24 h prior to cell harvesting, and gene expression levels were determined. Results (mean±SD of replicate determinations) are expressed relative to the transcript levels detected in the cells at the initiation of the cultures. Error bars (SD) smaller than the size of the symbol are not shown.
Figure 8:
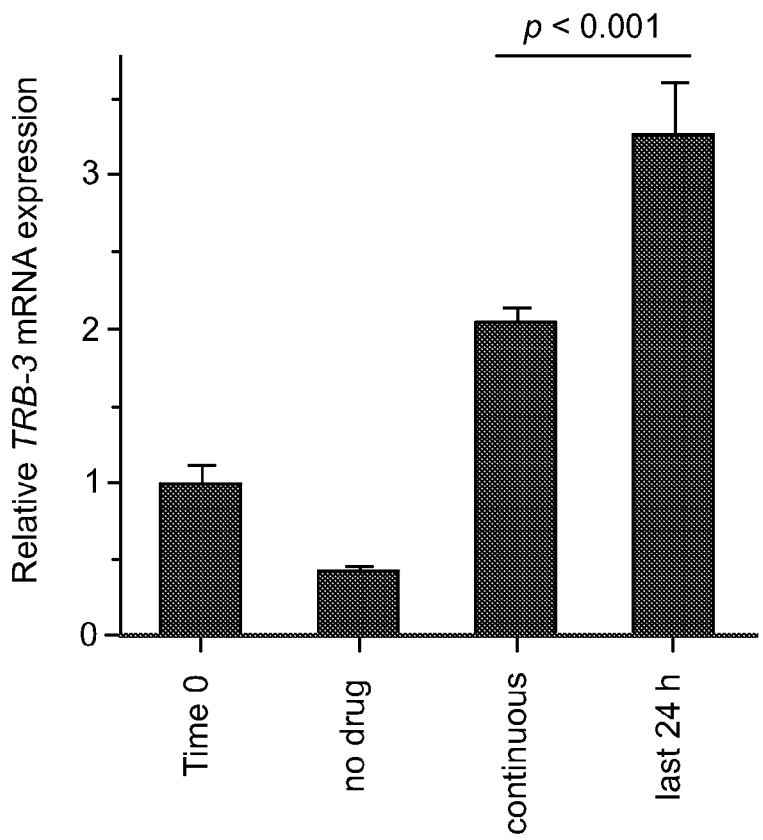
FIG. 8 shows a comparison of the TRB-3 response as a result of continuous or short term exposure to anagrelide. Expanded CD34+ cells were grown for 4 days under standard megakaryocyte culture conditions in the absence or presence of 1 µM anagrelide. The drug was added either at the initiation of the cultures (continuous) or 24 h prior to cell harvesting (last 24 h), and gene expression levels were determined. Results (mean±SD of replicate determinations) are expressed relative to the transcript levels detected in the cells at the initiation of the cultures (time 0). Error bars (SD) smaller than the size of the symbol are not shown. Where indicated statistical significance was determined by ANOVA with Bonferroni's post hoc test.

As shown in FIG. 7 when exposure to anagrelide was confined to the initial 2-3 days of culture the response to the drug was relatively weak. However, following this refractory phase the cells responded with a sharp increase in TRB-3 expression, even though the period of exposure to the drug was kept to the same length (i.e., 24 h). Strikingly, as shown in FIG. 8, treatment for 24 h with anagrelide following three days of culture in its absence resulted in a higher level of TRB-3 expression than if the drug was present for the entire four day period of culture. This difference in the magnitude of the response is consistent with a "feed-back type mechanism" in which TRB-3 would inhibit also its own expression, thus resulting in a "dampening" of the response to the test agent. These results exemplify the presence of a 24 h window (e.g. between days 3 and 4 of the megakaryocyte culture) in which the sensitivity of the assay is increased. Furthermore, a modified version of the assay incorporating this shorter period of incubation with test agents may be useful for the screening of compounds which are less stable in aqueous media.

Example 3

To further substantiate the validity of TRB-3 expression as a read-out for the identification of candidate agents affecting megakaryocyte development, work described below investigated the role of TRB-3 in megakaryocytopoiesis using RNA interference technology.

Materials and Methods

Cell Transduction and Analysis of Transduced Cells

UT7/mpl cells (clone 5.1) (Goncalves et al., *Leukemia* 12:1355-1366 (1998)) or human umbilical cord blood CD34+ hematopoietic cells were infected with pLKO.1-puro lentiviral vectors carrying short hairpin (sh) RNA sequences against human TRB-3 (designated shTRB3.1 to shTRB3.5) or a non-targeting scramble shRNA (designated shControl). shRNA clones were purchased from Sigma.

UT7/mpl cells were grown in Iscove's modified Dulbecco's medium in the presence of 2.5 ng/ml GM-CSF as previously described (Ahluwalia et al., *J. Thromb. Haemost*. Epub ahead of print, 25 June, DOI: 10.1111/j.1538-7836.2010.03970.x2010). Infections were carried out in the presence of 4 µg/ml polybrene by spinoculation at 900 g for 30 min at 21° C., followed by overnight incubation at 37° C. Infected cells were selected with 1 µg/ml puromycin.

Expanded CD34+ cells (see Materials and Methods Section of Example 1) were infected as described above and then were sub-cultured under standard megakaryocyte culture conditions with anagrelide or an equivalent amount of vehicle for 2 days prior to addition of 1 µg/ml puromycin and further differentiation for 5 days.

CD61 expression of live cells was analysed by flow cytometry following double staining with 7-amino actinomycin D and the FITC-conjugated monoclonal antibody Y2/51 (Dako cytomation) or an isotype-matched control antibody; the latter was used to set a boundary between positive and negative cells.

Results

Figure 9:
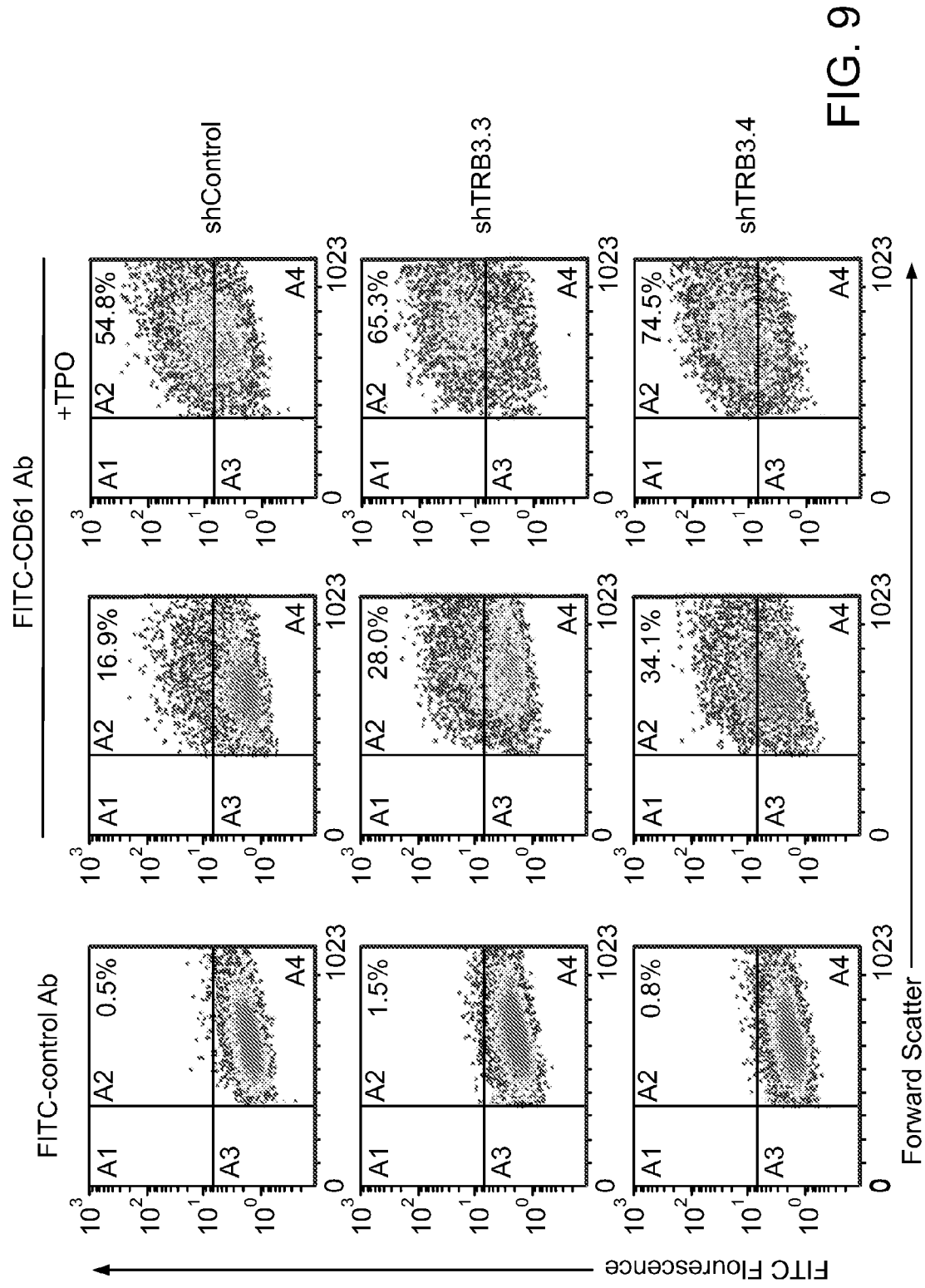
FIG. 9 shows flow cytometric density plots of CD61 expression (FITC Fluorescence) vs Forward Scatter for UT7/mpl cells transduced with TRB3 or Control shRNAs following culture in the absence or presence of TPO. UT7/mpl cells were infected overnight with shTRB3.3, shTRB3.4 or shControl. Following selection with 1 µg/ml puromycin, the transduced cells were grown for 7 days in the absence or presence of 100 ng/ml TPO as indicated. CD61 expression was analysed by flow cytometry as described in Example 3 herein. Values represent the percentage of CD61+ cells.
Figure 10:
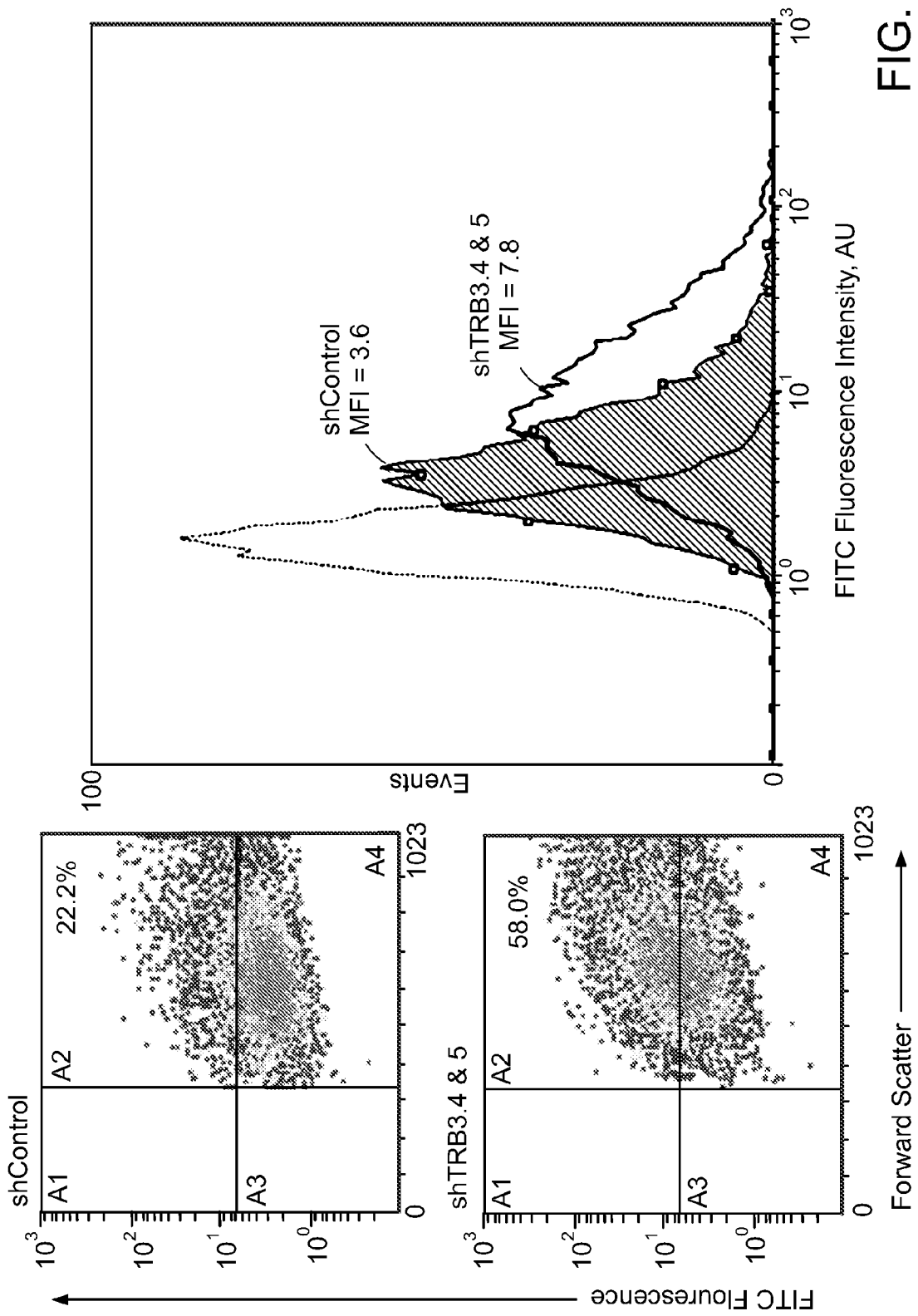
FIG. 10 shows a flow cytometric analysis of CD61 expression for UT7/mpl cells transduced with TRB3 or Control shRNAs following culture in presence of TPO. UT7/mpl cells were infected overnight with shControl or with a mixture of shTRB3.4 and shTRB3.5. Following selection with 1 µg/ml puromycin, the transduced cells were grown for 3 days in the presence of 100 ng/ml TPO. CD61 expression was analysed by flow cytometry as described in Example 3 herein. Density plots of CD61 expression (FITC Fluorescence) vs Forward Scatter depict the percentage of CD61+ cells. Histogram plots depict the relative levels of CD61 expression in shTRB3 and shControl-transduced cells. The values next to the peaks represent the median fluorescence intensities of the respective cell populations. The dotted trace corresponds to the fluorescence distribution of a sample stained with the control antibody.

Five pLKO.1-puro-TRB3 shRNA constructs (designated shTRB3.1 to shTRB3.5) were initially tested for their ability to affect expression of the megakaryocytic differentiation marker CD61 in UT7/mpl cells. Compared to a control shRNA, four of the TRB3 shRNAs constructs efficiently increased the fraction of CD61+UT7/mpl cells, under both basal and TPO-stimulated conditions. FIG. 9 shows results for shTRB3.3 and shTRB3.4 after seven days of culture. Similar results were obtained with shTRB3.2 and shTRB3.5 (data not shown). It was also observed that if the cells were cultured with TPO for a shorter period of time (3 days instead of 7 days), there was a synergistic effect between TRB-3 silencing and the hormone on the differentiation of these cells (FIG. 10).

This work further assessed whether TRB-3 silencing interfered with the inhibitory effect of anagrelide on megakaryocyte development of primary hematopoietic progenitor cells. To this end expanded CD34+ cells were infected with shTRB3 or shControl and compared the response to the drug following incubation under standard megakaryocyte culture conditions. As shown in Table 1 TRB-3 silencing reduced the ability of anagrelide-to inhibit megakaryocyte growth by more than half.

TABLE 1

|           | MK cell number, ×$10^3$ | | Inhibition |
|-----------|------|-----------|------|
|           | DMSO | Anagrelide | %    |
| shControl | 209  | 106       | 49.3 |
| shTRB3    | 257  | 202       | 21.5 |

Table 1 illustrates the effect of TRB-3 silencing on the ability of anagrelide-to inhibit megakaryocyte growth in cultures of primary hematopoietic progenitor cells. Expanded CD34+ cells were infected overnight with shControl or with a mixture of shTRB3.4 and shTRB3.5. Cells were then cultured for one week in the presence of anagrelide or an equivalent amount of vehicle under standard megakaryocyte culture conditions, except that 1 ug/ml puromycin was added after 2 days. The number of megakaryocytic cells was determined by cell counting of viable cells and flow cytometry.

Taken together these results demonstrate that TRB-3 is a negative modulator of megakaryocyte development, thus providing a biological rationale for its use as a marker for the discovery of agents affecting megakaryocyte development.

What is claimed is:

1. A method of identifying an anti-megakaryocyte agent comprising:
    contacting, a cell capable of expressing TRB-3 with an agent to be tested for anti-megakaryocyte activity;
    measuring expression of TRB-3 in a cell contacted with the test agent;
    comparing the expression of TRB-3 in a cell contacted with the test agent to a control level of expression;
    assessing the anti-megakaryocyte activity of a test agent which increases the expression of TRB-3 in a cell contacted with the test agent relative to the control level of expression,
    identifying a test agent having anti-megakaryocyte activity as an anti-megakaryocyte agent.

2. The method according to claim 1 wherein the cell endogenously expresses TRB-3.

3. The method according to claim 1 wherein the cell is a hematopoietic progenitor cell.

4. The method according to claim 1 wherein the cell is a megakaryocyte.

5. The method according to claim 1 wherein the cell is a mammalian cell.

6. The method according to claim 1 wherein the cell is a human cell.

7. The method according to claim 1 wherein TRB-3 expression is measured by measuring a TRB-3 expression product.

8. The method according to claim 1 wherein TRB-3 expression is measured by measuring TRB-3 mRNA.

9. The method according to claim 8 wherein TRB-3 mRNA expression is measured using one or more methods selected from the group consisting of polymerase chain reaction, reverse-transcribed polymerase chain reaction, and quantitative polymerase chain reaction.

10. The method according to claim 8 wherein TRB-3 mRNA expression is measured using mass spectrometry.

11. The method according to claim 8 wherein TRB-3 mRNA expression is measured using microarrays.

12. The method according to claim 1 wherein TRB-3 expression is measured by measuring TRB-3 polypeptide.

13. The method according to claim 1 wherein the control level of expression is the level of expression of TRB-3 in a cell in the absence of the test agent.

14. The method according to claim 1 wherein a test agent which increases expression of TRB-3 in a cell contacted with said agent at least 2-fold relative to the control level of expression is a candidate anti-megakaryocyte agent.

15. The method according to claim 1 wherein absolute expression of TRB-3 is measured.

16. The method according to claim 1 wherein expression of TRB-3 is measured relative to an endogenous reference gene.

17. The method according to claim 16 wherein the endogenous reference gene is TBP or GUSB.

18. The method according to claim 17 wherein a test agent which increases expression of TRB-3 at least about 2-fold is a candidate anti-megakaryocyte agent.

19. A method of identifying a candidate anti-megakaryocyte agent comprising:
    contacting, a cell capable of expressing TRB-3 and GpIIb with an agent to be tested for anti-megakaryocyte activity;
    measuring expression of TRB-3 and GpIIb in a cell contacted with the test agent;
    comparing the expression of TRB-3 and GpIIb in a cell contacted with the test agent to a control level of expression;
    wherein a test agent which increases expression of TRB-3 without significantly increasing expression of GpIIb in a cell contacted with the test agent relative to the control level of expression is a candidate anti-megakaryocyte agent.

20. The method according to claim 19 wherein a test agent which increases expression of TRB-3 and reduces expression of GpIIb relative to expression of GpIIb typical of megakaryocyte differentiation is a candidate anti-megakaryocyte agent.

21. The method according to claim 19 further comprising determining the ratio of TRB-3 expression to GpIIb expression, and wherein a test agent which increases said expression ratio by at least about 2.5-fold is a candidate anti-megakaryocyte agent.

22. The method according to claim 19 wherein the cell endogenously expresses TRB-3 and GpIIb.

23. The method according to claim 19 wherein the cell is a hematopoietic progenitor cell.

24. The method according to claim 19 wherein the cell is a megakaryocyte.

25. The method according to claim 19 wherein the cell is a mammalian cell.

26. The method according to claim 19 wherein the cell is a human cell.

27. The method according to claim 19 wherein TRB-3 expression is measured by measuring a TRB-3 expression product.

28. The method according to claim 19 wherein TRB-3 expression is measured by measuring TRB-3 mRNA.

29. The method according to claim 19 wherein GpIIb expression is measured by measuring GpIIb mRNA.

30. The method according to claim 19 wherein TRB-3 expression is measured by measuring TRB-3 polypeptide.

31. The method according to claim 19 wherein GpIIb expression is measured by measuring GpIIb polypeptide.

32. The method according to claim 1 further comprising screening an identified anti-megakaryocyte agent for additional properties.

33. The method according to claim 20 further comprising screening an identified candidate anti-megakaryocyte agent for additional properties.

34. A method of identifying an agent for inhibiting differentiation of megakaryocytes comprising:
   contacting, a cell capable of expressing TRB-3 with an agent to be tested for inhibiting differentiation of megakaryocytes;
   measuring expression of TRB-3 in a cell contacted with the test agent;
   comparing the level of expression of TRB-3 in a cell contacted with the test agent to a control level of expression;
   assessing the anti-megakaryocyte activity of a test agent which increases expression of TRB-3 in a cell contacted with the test agent relative to the control level of expression,
   identifying a test agent having anti-megakaryocyte activity as an agent for inhibiting differentiation of megakaryocytes.

35. The method according to claim 34 wherein the cell is a hematopoietic progenitor cell.

36. A method of identifying a candidate agent for inhibiting differentiation of megakaryocytes comprising:
   contacting, a cell capable of expressing TRB-3 and GpIIb with an agent to be tested for inhibiting differentiation of megakaryocytes;
   measuring expression of TRB-3; and GpIIb in a cell contacted with the test agent;
   comparing the expression of TRB-3 and GpIIb in a cell contacted with the test agent with a control level of expression; wherein a test agent which increases the expression of TRB-3 without significantly increasing the expression of GpIIb in a cell contacted with the test agent relative to the control level of expression is a candidate agent for inhibiting differentiation of megakaryocytes.

37. The method according to claim 36 further comprising determining the ratio of TRB-3 expression to GpIIb expression, and wherein a test agent which increases said expression ratio by at least about 2.5-fold is a candidate agent for inhibiting differentiation of megakaryocytes.

38. The method according to claim 36 wherein the cell is a hematopoietic progenitor cell.

39. The method according to claim 34, wherein the cell is capable of megakaryocyte differentiation.

40. The method according to claim 39, wherein the contacting is performed after megakaryocyte differentiation has begun.

* * * * *